US012773157B2

(12) United States Patent
Sakemi

(10) Patent No.: US 12,773,157 B2
(45) Date of Patent: Oct. 27, 2026

(54) DETERMINATION DEVICE, DETERMINATION METHOD, AND STORAGE MEDIUM

(71) Applicant: NEC Corporation, Tokyo (JP)

(72) Inventor: Yusuke Sakemi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 236 days.

(21) Appl. No.: 18/684,893

(22) PCT Filed: Sep. 3, 2021

(86) PCT No.: PCT/JP2021/032562

§ 371 (c)(1),
(2) Date: Feb. 20, 2024

(87) PCT Pub. No.: WO2023/032178

PCT Pub. Date: Mar. 9, 2023

(65) Prior Publication Data

US 2025/0127451 A1 Apr. 24, 2025

(51) Int. Cl.
*A61B 5/364* (2021.01)

(52) U.S. Cl.
CPC .................................... *A61B 5/364* (2021.01)

(58) Field of Classification Search
CPC .......... A61B 5/364; G06N 3/09; G06N 3/044; G16H 50/20
See application file for complete search history.

(56) References Cited

U.S. PATENT DOCUMENTS

2015/0190068 A1* 7/2015 Cole ...................... A61B 5/349
600/509
2017/0112401 A1* 4/2017 Rapin .................... A61B 5/316
2018/0368723 A1* 12/2018 Ibáñez Català ........ A61B 5/361

FOREIGN PATENT DOCUMENTS

JP 2018-000224 A 1/2018
JP 2020-528295 A 9/2020
WO 2020/194591 A1 10/2020

OTHER PUBLICATIONS

JP Official Communication for JP Application No. 2024-513683, mailed on Mar. 5, 2025 with English Translation.
Fatemeh Hadaeghi, "Reservoir Computing Models for Patient-Adaptable ECG Monitoring in Wearable Devices", arXiv [online], 2019, p. 1-27, [Feb. 21, 2025 search], Internet <URL: https://arxiv.org/abs/1907.09504v1>, 1907.09504v1.
JP Office Action for JP Application No. 2024-513683, mailed on Oct. 8, 2024 with English Translation.
International Search Report for PCT Application No. PCT/JP2021/032562, mailed on Nov. 16, 2021.

(Continued)

*Primary Examiner* — Catherine M Voorhees
(74) *Attorney, Agent, or Firm* — Sughrue Mion, P.LLC

(57) ABSTRACT

A determination device includes a memory configured to store instructions and a model for receiving an input of data relating to a determination target for each time step and for changing the state thereof for each time step. The determination device further includes a processor configured to execute the instructions to: identify a reference time step as a time step serving as the reference to the changing state of the determination target, and perform determination of the determination target based on the state of the model at a derivative time step from the reference time step.

9 Claims, 6 Drawing Sheets

(56) References Cited

OTHER PUBLICATIONS

Written opinion for PCT Application No. PCT/JP2021/032562, mailed on Nov. 16, 2021.
Bauer F.C. et al., Real-Time Ultra-Low Power ECG Anomaly Detection Using anEvent-Driven Neuromorphic Processor, IEEE Transactions on Biomedical Circuitsand Systems[online], Nov. 11, 2019, vol. 13, No. 6, pp. 1575-1582.

* cited by examiner

DETERMINATION DEVICE, DETERMINATION METHOD, AND STORAGE MEDIUM

This application is a National Stage Entry of PCT/JP2021/032562 filed on Sep. 3, 2021, the contents of all of which are incorporated herein by reference, in their entirety.

TECHNICAL FIELD

The present invention relates to a determination device, a determination method, and a storage medium.

BACKGROUND ART

It has been proposed that neural networks can be used for processes for determining the existence/nonexistence of a heart abnormality using electrocardiograms (ECGs). For example, Patent Document 1 discloses a method of determining the existence/nonexistence of an abnormality using convolutional neural networks applied to ECGs represented by matrixes having real numbers.

CITATION LIST

Patent Literature

PTL 1: U.S. Patent Application Publication No. 2017/0112401

SUMMARY OF INVENTION

Technical Problem

It is expected that convolutional neural networks capable of partially performing convolutional computation with input data can be used to detect time-series data partially having features with relatively high accuracy. Generally speaking, convolutional neural networks require large amounts of calculations, which in turn require devices having high computation performance. It is expected that some devices may require relatively small amounts of calculations if they can handle time-series data partially having features without using convolutional neural networks.

One exemplary objective of the present invention is to provide a determination device, a determination method, and a storage medium which can solve the aforementioned problem.

Solution to Problem

In a first aspect of the present invention, a determination device includes a state change means for receiving an input of data relating to a determination target for each time step and for changing the state thereof for each time step, a reference-time-step identifying means for identifying a reference time step as a time step serving as the reference to the changing state of the determination target, and a determination means for performing determination of the determination target based on the state of the state change means at a derivative time step from the reference time step.

In a second aspect of the present invention, a determination method causing a device equipped with a state change means for receiving an input of data relating to a determination target for each time step and for changing the state thereof for each time step to implement identifying a reference time step as a time step serving as the reference to the changing state of the determination target, and performing determination of the determination target based on the state of the state change means at a derivative time step from the reference time step.

In a third aspect of the present invention, a storage medium has a stored program causing a device equipped with a state change means for receiving an input of data relating to a determination target for each time step and for changing the state thereof for each time step to execute identifying a reference time step as a time step serving as the reference to the changing state of the determination target, and performing determination of the determination target based on the state of the state change means at a derivative time step from the reference time step.

Advantageous Effects of the Invention

According to the present invention, it is possible to handle time-series data partially having features without requiring convolutional neural networks.

DESCRIPTION OF EMBODIMENTS

Hereinafter, an exemplary embodiment of the present invention will be described below. However, the exemplary embodiment may not limit the scope of the invention defined by the appended claims. In addition, all the combinations of features described in the exemplary embodiment may not be necessarily essential to the solving means of the invention.

Figure 1:
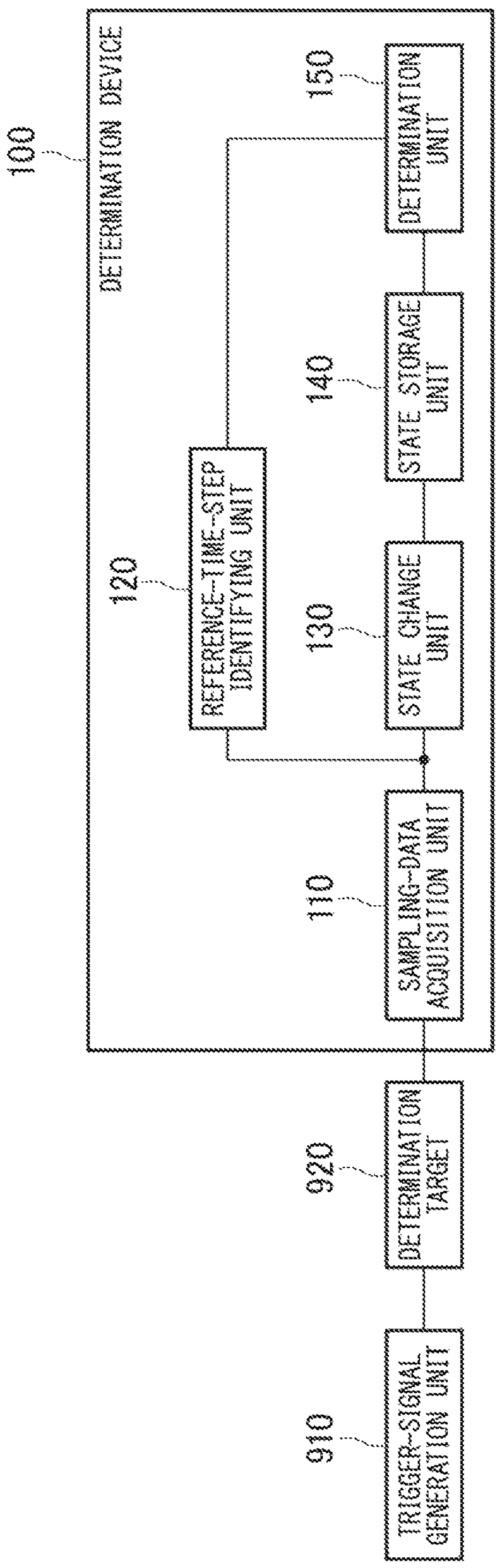
FIG. 1 shows an example in which a reference-time-step identifying unit 120 is configured to identify reference time steps based on sampling data from a sampling-data acquisition unit 110.

FIG. 1 shows a configuration example of a determination device according to the exemplary embodiment. According to the configuration shown in FIG. 1, the determination device 100 includes a sampling-data acquisition unit 110, a reference-time-step identifying unit 120, a state change unit 130, a state storage unit 140, and a determination unit 150.

The determination device 100 is configured to make determination of the determination target 920. In particular, the determination device 100 may determine the determination-execution timing based on a timing relating to the state of the determination target 920 when its state is changed.

Hereinafter, descriptions will be made with respect to an example of the determination device 100 configured to determine the existence/nonexistence of a heart abnormality of a heart serving as the determination target 920 based on electrocardiogram data. In this connection, the determination target 920 to be determined by the determination device 100 is not necessarily limited to specific types of objects; hence, it is possible to determine any values to be varied due to changing states with respect to any types of measurable objects.

For example, it is possible to apply the determination target 920 to any types of objects which can be classified in movements such as factory machines and human species.

The trigger-signal generation unit 910 is configured to output a signal triggering a changing state of the determination target 920. Herein, a signal triggering a changing state of the determination target 920 will be referred to as a trigger signal. As to a heart serving as the determination target 920, it is possible to mention a sinoatrial node as an example of the trigger signal generation unit 910.

The sampling-data acquisition unit 110 is configured to measure values relating to the determination target 920. For example, the sampling-data acquisition unit 110 may be equipped with a sensor configured to measure the output of the determination target 920 or the state of the determination target 920, thus outputting measurement values as sensing data.

The sampling-data acquisition unit 110 may directly measure the determination target 920 or indirectly measure the determination target 920 by measuring temperatures in ambient environments of the determination target 920. Direct measurements of the determination target 920 and indirect measurements of the determination target 920 will be collectively referred to as measurements of the determination target 920.

The sampling-data acquisition unit 110 may be included in the determination device 100 or the determination target 920. Alternatively, the sampling-data acquisition unit 110 may be configured outside of the determination device 100 and outside of the determination target 920. FIG. 1 shows an example of the sampling-data acquisition unit 110 which is included in the determination device 100.

When the determination device 100 is configured to determine the existence/nonexistence of a heart abnormality using electrocardiograms, the sampling-data acquisition unit 110 may be made up of an electrocardiograph configured to measure electrocardiogram data for each predetermined period and to output measured data as sampling data. For example, electrocardiogram data may be measured data of potentials (or potential differences) between electrodes of an electrocardiograph.

Figure 2:
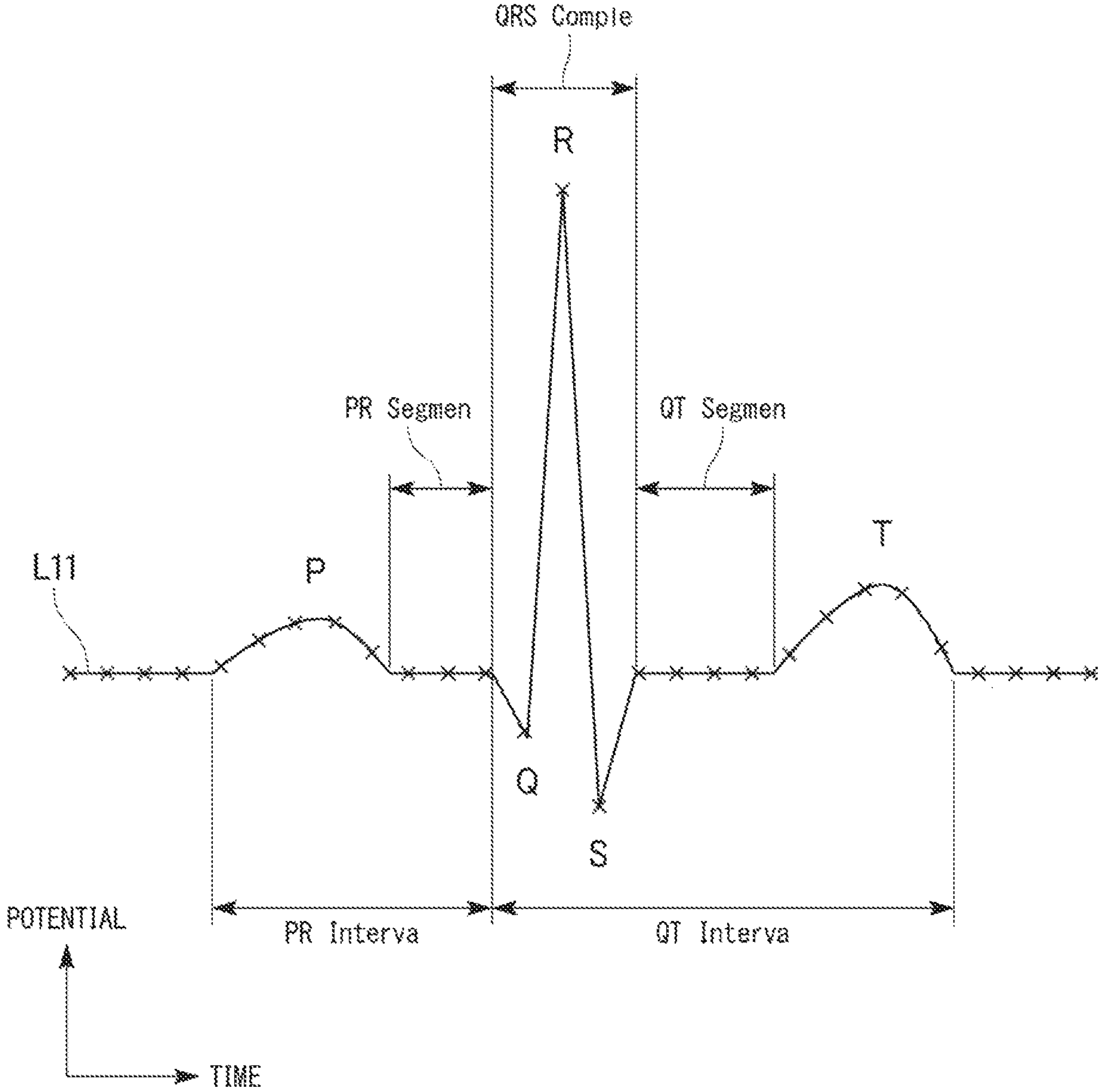
FIG. 2 shows an example of electrocardiogram data acquired by the sampling-data acquisition unit 110.

FIG. 2 shows an example of electrocardiogram data acquired by the sampling-data acquisition unit 110. In the graph of FIG. 2, the horizontal axis represents time while the vertical axis represents potentials.

A line L11 indicates an example of an electrocardiogram. Symbols "x" plotted on the line L11 indicate examples of data sampled as electrocardiogram data.

FIG. 2 shows an example of the sampling-data acquisition unit 110 configured to perform sampling of electrocardiogram data for each constant period.

Sampling periods of electrocardiogram data acquired by the sampling-data acquisition unit 110 are not necessarily limited to specific time intervals. When the sampling-data acquisition unit 110 is configured to accurately measure the local maximum and the local minimum of potentials, for example, the sampling-data acquisition unit 110 may perform sampling in shorter time intervals.

Hereinafter, Δt denotes a sampling period for acquiring electrocardiogram data with the sampling-data acquisition unit 110. The following descriptions may refer to time as a time step for each time Δt. In this connection, individual steps of time steps may be simply referred to as time steps or time of time steps.

For example, t−Δt denotes a previous time step which is one-step before a time step t. In addition, t+Δt denotes a next time step which is next to a time step t. The previous time step before the time step t is a past time step which is one-step past the time step t. The next time step next to the time step t is a future time step which is one-step after the time step t.

The sampling-data acquisition unit 110 is configured to acquire sampling data of an electrocardiogram for each time step.

FIG. 2 shows an electrocardiogram for one heartbeat. As shown in FIG. 2, a typical electrocardiogram observes a series of waveforms sequentially appearing in an order of a P-wave, a Q-wave, an R-wave, an S-wave, and a T-wave. The P-wave, the R-wave, and the T-wave indicate the local maximum of potentials. On the other hand, the Q-wave and the S-wave indicate the local minimum of potentials. The Q-wave, the R-wave, and the S-wave will be collectively referred to as a QRS complex.

The time after starting the P-wave before starting the Q-wave will be referred to as a PR interval of time. The time after starting the Q-wave before ending the T-wave will be referred to as a QT interval of time. The time after ending the P-wave before starting the Q-wave will be referred to as a PR segment. The time after ending the S-wave before starting the T-wave will be referred to as an ST segment.

An electrocardiogram section can be associated with a heart section. For example, the P-wave represents an atrial systole, the QSR complex represents a ventricular systole, and the T-wave represents recovery from a ventricular systole.

The sampling-data acquisition unit 110 is configured to output data representing measurement values which can be obtained by measuring the determination target 920. The sampling data output from the sampling-data acquisition unit 110 will be referred to as determination-target-related data or simply referred to as sampling data.

In particular, the sampling-data acquisition unit 110 is able to acquire and output time-series data of sampling data by performing measurement of the determination target 920 for each sampling period. The time-series data of sampling data output from the sampling-data acquisition unit 110 will be referred to as determination-target-time-series data.

The reference-time identifying unit 120 is configured to identify a reference time step. The reference-time step is a time step serving as reference pertaining to the changing state of the determination target 920. When the state of the determination target 920 is changed periodically, for example, the reference-time-step identifying unit 120 may identify a reference time step as a time step including a predetermined timing in one period of changing the state of the determination target 920.

The reference time step identified by the reference-time-step identifying unit 120 is used as a standard time step for the determination unit 150 of the determination device 100 to make determination of the determination target 920 at a specific time step according to the changing state of the determination target 920.

The reference-time-step identifying unit 120 indicates an example of a reference-time-step identifying means.

The reference-time-step identifying unit 120 may directly detect a trigger signal. For example, the trigger-signal generation unit 910 may be located outside the determination target 920 such that the reference-time-step identifying unit 120 can detect a trigger signal output from the trigger-signal generation unit 910.

Figure 3:
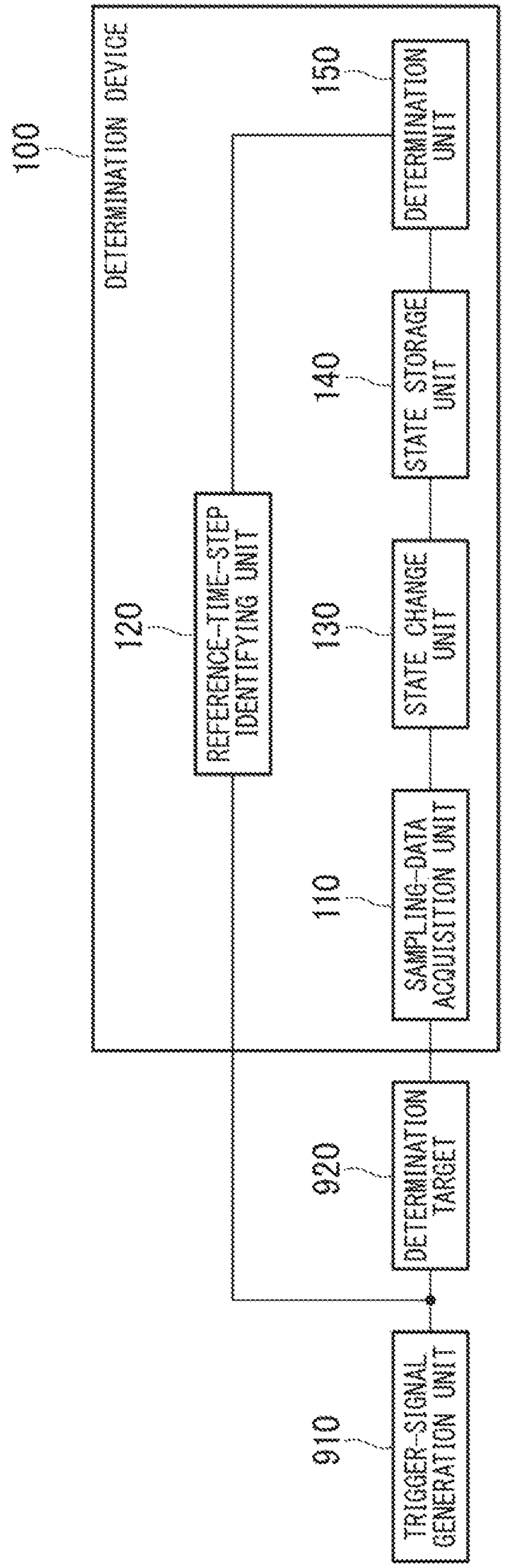
FIG. 3 shows a configuration example of a determination device 100 in which the reference-time-step identifying unit 120 is configured to directly detect a trigger signal from a trigger-signal generation unit 910.

FIG. 3 shows a configuration example of the determination device 100 in which the reference-time-step identifying unit 120 is configured to directly detect a trigger signal from the trigger-signal generation unit 910.

The configuration example of FIG. 3 differs from the configuration example of FIG. 1 in that the reference-time-step identifying unit 120 is configured to acquire a trigger signal from the trigger-signal generation unit 910 instead of sampling data from the sampling-data acquisition unit 110. In other aspects, the configuration of the determination device 100 shown in FIG. 3 is identical to the configuration shown in FIG. 1.

As an example of the trigger-signal generation unit 910 located outside the determination target 920, it is possible to mention a device using an external clock such as an audio system using an external clock; but this is not a restriction.

When the reference-time-step identifying unit 120 is configured to detect a trigger signal from the trigger-signal generation unit 910, it is possible to identify a reference time step as a time step for inputting a trigger signal to the reference-time-step identifying unit 120. Alternatively, when it takes a long time to detect a trigger signal, the reference-time-step identifying unit 120 may identify a reference time step as a next time step next to a time step for inputting a trigger signal to the reference-time-step identifying unit 120.

A time step and its associated time step, which is shifted from the time step by a predetermined number of time steps, will be each referred to as a derivative time step from the time step. The reference-time-step identifying unit 120 may identify a reference time step corresponding to a time step for inputting a trigger signal to the reference-time-step identifying unit 120.

It may be difficult or not possible for the reference-time-step identifying unit 120 to directly detect a trigger signal. As an example of incapacity or difficulty for the reference-time-step identifying unit 120 to directly detect a trigger signal, it is possible to mention an example of incapacity or difficulty to directly observe the trigger-signal generation unit 910. As an example of incapacity or difficulty to directly detect a trigger signal, it is possible to mention an example of incapacity or difficulty to detect a weak trigger signal.

When the determination target 920 is a heart while the trigger-signal generation unit 910 is a sinoatrial node which may exist inside a human body and which may output a weak electric signal, it is difficult to directly detect an electric signal output from a sinoatrial node in a noninvasive manner. Generally speaking, it is unrealistic to noninvasively detect an electric signal output from a sinoatrial node.

Even when the reference-time-step identifying unit 120 cannot directly detect a trigger signal, it is possible to identify a reference time step based on sampling data from the sampling-data acquisition unit 110. FIG. 1 shows an example of the reference-time-step identifying unit 120 configured to identify a reference time step based on sampling data from the sampling-data acquisition unit 110.

In this case, the reference-time-step identifying unit 120 may detect sampling data corresponding to characteristic parts of determination-target-time-series data. Subsequently, the reference-time-step identifying unit 120 may identify a reference time step as a time step for detecting sampling data corresponding to characteristic parts. Accordingly, it is expected that the reference-time-step identifying unit 120 can detect sampling data corresponding to characteristic parts with high accuracy, thus minimizing a possibility of failing to identify a reference time step.

In the configuration example of FIG. 2 in which the reference-time-step identifying unit 120 is configured to detect R-wave sampling data, it is expected that sampling data can be detected with high accuracy since a large potential difference lies between sampling data and its fore-and-aft sampling data.

It is possible to determine the R-wave sampling data when the reference-time-step identifying unit 120 compares a sampling-data value (i.e., a measured potential value) with a predetermined threshold value to determine that the sampling-data value is equal to or above the threshold value.

In this case, a condition in which the sampling-data value is equal to or above the threshold value may serve as an example of a predetermined condition. In addition, a time step in which the sampling-data value becomes equal to or above the threshold value may serve as an example of a time step relating to data of the determination target 920 meeting the predetermined condition.

Alternatively, the reference-time-step identifying unit 120 may identify a reference time step based on both a trigger signal from the trigger-signal generation unit 910 and determination-target-time-series data from the determination target 920. When the trigger-signal generation unit 910 generates a weak trigger signal, the reference-time-step identifying unit 120 may identify a reference time step based on both the trigger signal from the trigger-signal generation unit 910 and the determination-target-time-series data from the determination target 920. Accordingly, it is expected that a possibility of the reference-time-step identifying unit 120 failing to identify a reference time step can be reduced.

The reference-time-step identifying unit 120 may perform learning about a process for detecting sampling data corresponding to characteristic parts of determination-target-time-series data.

The aforementioned learning refers to adjustment of parameter values in a learning model. For example, it is possible to input sampling data into a deterministic equation which may allow the reference-time-step identifying unit 120 to determine whether or not sampling data corresponds to characteristic parts of determination-target-time-series data. In this case, the deterministic equation may serve as an example of a learning model, wherein adjusting parameter values such as factors of the deterministic equation may serve as an example of learning.

The state change unit 130 is configured to accept an input of sampling data from the sampling-data acquisition unit 110. The state change unit 130 provides a state such that the state of the state change unit 130 may be changed due to an input of sampling data. The state change unit 130 accepts an input of sampling data for each time step such that the state change unit 130 may experience a change of its state for each time step.

In this connection, the state change unit 130 may serve as an example of a state change means.

The state change unit 130 may be formulated as a reservoir layer in reservoir computing. That is, the state change unit 130 may be formed using a recurrent neural network (RNN). In this connection, it is possible to set in advance that the internode weighting factors of the state change unit 130 will be exempted from learning. For example, it is possible to randomly set in advance the internode connections and the weighting factors of the state change unit 130.

Owing to the recurrent configuration of the state change unit 130, the state of the state change unit 130 may reflect not only the current state of the determination target 920 but also the past state of the determination target 920.

Math. (1) expresses a state x(t) of a reservoir layer of reservoir computing at a time step t.

[Math. 1]

$$x(t)=f\left(W^{res}x(t-\Delta t)+W^{in}u(t)\right) \tag{1}$$

In the above, the term x(t−Δt) indicates the state of a reservoir layer at the time step t−Δt. As described above, the time step t−Δt is a time step which is one time step before the time step t. Both the symbols x(t) and x(t−Δt) can be expressed as column vectors each having the number of elements identical to the number of nodes in a reservoir layer.

In the above, the symbol $W^{res}$ is a matrix representing weighting factors for weighting values of intermediate nodes. In Math. (1), the term "$W^{res}$x(t−Δt)" represents weighting values of intermediate nodes at the time step t−Δt. The matrix $W^{res}$ is a square matrix having the number of rows and the number of columns both identical to the number of elements in a vector x(t). The calculation result of "$W^{res}$x(t−Δt)" can be expressed as a column vector having the number of elements identical to the number of elements of the vector x(t).

The symbol u(t) is a vector representing input values of a reservoir computing system at the time step t. The vector u(t) is expressed as a column vector.

The symbol $W^{in}$ is a matrix representing weighting factors applied to input values. In Math. (1), the term "$W^{in}$u(t)" represents weighting of input values at the time step t. The number of rows of the matrix $W^{in}$ is identical to the number of elements of the vector x(t) while the number of columns of the matrix $W^{in}$ is identical to the number of elements of the vector u(t). The calculation result of the term "$W^{in}$u(t)" is expressed as a column vector having the number of elements identical to the number of elements of the vector x(t).

The symbol f represents an activation function. The calculation result of the term "$W^{res}$x(t−Δt)+$W^{in}$u(t)" is expressed as a column vector having the number of elements identical to the number of elements of the vector x(t), and therefore the term "f($W^{res}$x(t−Δt)+$W^{in}$u(t))" indicates that the activation function is applied to each of the elements of the column vector.

An output y(t) of a reservoir computing system at the time step t is expressed by Math. (2).

[Math. 2]

$$y(t)=W^{out}x(t) \tag{2}$$

In the above, the symbol $W^{out}$ is a matrix representing weighting factors used in weighting operations to produce an output value from values of intermediate nodes. The number of rows of the matrix $W^{out}$ is identical to the number of elements of the vector y(t) while the number of columns of the matrix $W^{out}$ is identical to the number of elements of the vector x(t). The term "$W^{out}$x(t)" indicates a weighted addition applied to values of intermediate nodes for each output node at time t.

In the determination device 100, Math. (2) and Math. (3) are modified and used for the determination of the determination target 920. The determination method of the determination device 100 as to how to make determination of the determination target 920 is not necessarily limited to a specific method.

The state storage unit 140 is configured to store the past state of the state change unit 130. For example, the state storage unit 140 is configured to store the state of the state change unit 130 for predetermined time steps in the immediate past.

A combination of the state change unit 130 and the state storage unit 140 may be formulated as a reservoir layer.

Specifically, it is possible to provide a storage node used to store a node value for each of the nodes constituting the state change unit 130. In this case, it is possible to directly output to a storage node each node value among values of nodes constituting the state change unit 130 using an internode weighting factor "1". Accordingly, a storage node may store a node value of the state change unit 130 at a certain time step in its next time step.

To store node values of the state change unit 130 in a time period for multiple time steps, it is possible to serially connect (or daisy-chain) a plurality of storage nodes as the number of time steps. That is, it is possible to store node values of the state change unit 130 for a number of time steps as the number of storage nodes serially connected together since a node value is stored on a next storage node among serially-connected storage nodes every time each time step passes over.

The determination unit 150 is configured to make determination of the determination target 920 based on the state of the state change unit 130. In particular, the determination unit 150 is configured to make determination of the determination target 920 based on the state of the state change unit 130 at a derivative time step from the reference time step identified by the reference-time-step identifying unit 120. In this connection, the determination unit 150 may serve as an example of a determination means.

Using the determination unit 150 configured to make determination of the determination target 920 at a derivative time step from the reference time step, it is possible to anticipate an impact of an event of the determination target 920 to appear partly in certain time-step data.

For example, it is possible to assume the determination device 100 configured to determine the existence/nonexistence of a heart abnormality based on electrocardiogram data. In this case, it is possible to expect that a noteworthy part of an electrocardiogram may be restricted when determining the existence/nonexistence of abnormality occurring in a certain part of a heart according to an association between an electrocardiogram part and a heart part. In the case of an atrial fibrillation, for example, a P-wave may not apparently appear in an electrocardiogram. To detect abnormality, it is effective to pay attention to sampling data at the time step corresponding to the P-wave.

It is possible to assume that sampling data indicating abnormality and sampling data not impacted by abnormality may appear among multiple sampling data acquired by the sampling-data acquisition unit 110 depending on the time step.

In this case, it is possible to assume arguendo that the determination unit 150 might continuously output determination results indicating abnormality when making determination over all the time steps. Then, the determination unit 150 might inevitably output the same determination result at both the time step of sampling data indicating abnormality and the time step of sampling data not impacted by abnormality. Accordingly, it is expected that the determination unit 150 may be reduced in determination accuracy since the determination unit 150 might output the same determination result irrespective of a difference as to the existence/nonexistence of abnormality in input data.

For this reason, the reference-time-step identifying unit 120 is configured to identity a reference time step. The determination unit 150 is configured to make determination of the determination target 920 based on the state of the state change unit 130 at a derivative time step from the reference time step. Accordingly, it is possible for the determination unit 150 to make determination for each time step in which the determination target 920 indicates similar states. This makes it possible for the determination unit 150 to make determination with relatively high accuracy since the state change unit 130 may indicates similar states for each time step causing the determination unit 150 to make determination of the determination target 920.

When the reference-time-step identifying unit 120 makes an attempt to identify a reference time step upon detecting sampling data corresponding to characteristic parts of determination-target-time-series data, the reference time step may not necessarily match the time step causing an impact of abnormality in sampling data.

When the reference-time-step identifying unit 120 detects a reference time step as a time step for obtaining R-wave sampling data, for example, the reference time step may differ from the time step for obtaining P-wave sampling data impacted by an atrial fibrillation.

To handle a difference between time steps, the determination device 100 should reflect input data at the past time step onto the determination device 100 in its own state.

Specifically, the state change unit 130 having a recurrent configuration is configured to create the state reflecting the past state of the determination target 920. In addition, the state storage unit 140 is configured to store the past state of the state change unit 130.

It is possible for the determination unit 150 to make determination of the determination target 920 based on the state of the state change unit 130 at the past time step before the reference time step in addition to or instead of the state of the state change unit 130 at the reference time step.

In addition, the determination unit 150 may make determination of the determination target 920 based on the state of the state change unit 130 at the future time step after the reference time step.

Figure 4:
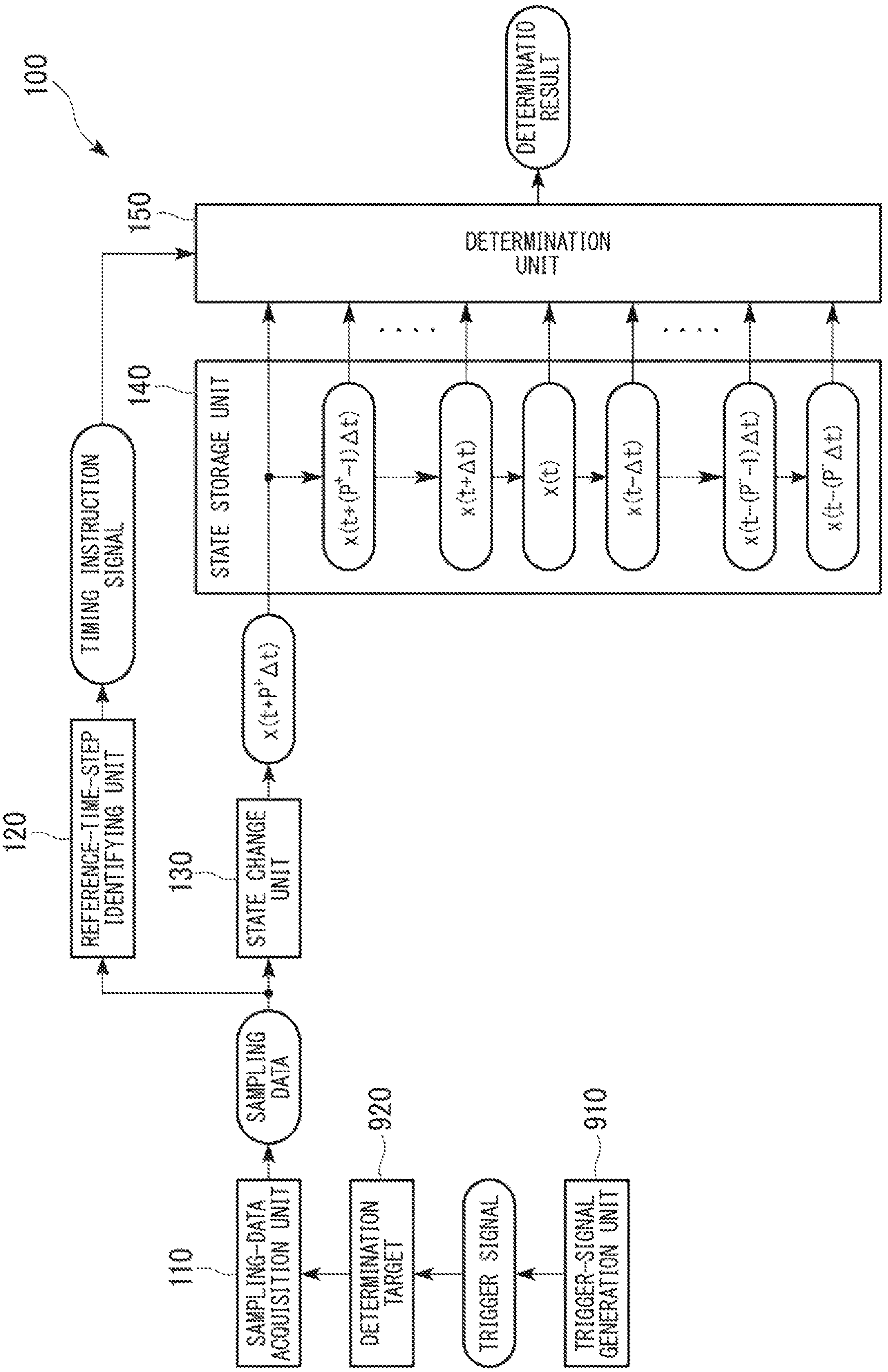
FIG. 4 shows an example of data flows in the determination device 100.

FIG. 4 shows an example of a data flow of the determination device 100.

In FIG. 4, the trigger-signal generation unit 910 outputs a trigger signal to the determination target 920. The state of the determination target 920 may be changed at a time step responsive to a trigger signal from the trigger-signal generation unit 910.

The sampling-data acquisition unit 110 performs measurement of the determination target 920 for each time step, thus acquiring sampling data. The sampling-data acquisition unit 110 acquires and outputs the sampling data to the reference-time-step identifying unit 120 and the state change unit 130. As described above, the reference-time-step identifying unit 120 may acquire a trigger signal from the trigger-signal generation unit 910 in addition to or instead of the sampling data. Since the state change unit 130 accepts an input of sampling data for each time step, the state change unit 130 may experience a change of the state for each time step. The state storage unit 140 stores the state of the state change unit 130 at the past time step.

In addition, the reference-time-step identifying unit 120 identifies a reference time step based on one of or both the sampling data and the trigger signal. The reference-time-step identifying unit 120 outputs a timing instruction signal to the determination unit 150 at a derivative time step from the identified reference time step. The timing instruction signal is used to instruct the time step for making determination of the determination target 920 with the determination unit 150.

In FIG. 4, the time step t represents a reference time step. In addition, the time step of $t+P^{+}\Delta t$ represents the current time step in FIG. 4. In this connection, $P^{+}$ denotes a constant expressed by a positive integer.

In FIG. 4, a combination of the state change unit 130 and the state storage unit 140 is configured to store the state of the state change unit 130 for each of time steps ranging from the time step $t-P^{-}\Delta t$ to the time step $t+P^{+}\Delta t$. Herein, $P^{-}$ is a constant expressed by a positive integer. The value of P may be identical to or different from the value of $P^{+}$.

The determination unit 150 makes determination of the determination target 920 based on the state of the state change unit 130 for each of time steps ranging from the time step $t-P^{-}\Delta t$ to the time step $t+P^{+}\Delta t$ according to the time step $t+P^{+}\Delta t$ responsive to the timing instruction signal from the reference-time-step identifying unit 120.

Now, the symbol $x\hat{}(t)$ denotes concatenated data formed by concatenating a series of data each representing the state of the state change unit 130 for each of time steps ranging from the time step $t-P^{-}\Delta t$ to the time step $t+P^{+}\Delta t$, while the symbol y(t) denotes the determination result of the determination unit 150. Using these symbols, for example, it is possible to express the determination of the determination unit 150 by Math. (3).

[Math. 3]

$$y(t)=Classfier(x\hat{}(t)) \tag{3}$$

In the above, the symbol "Classifier" denotes a classifier used for classification, and therefore Math. (3) shows an example of determination made by the determination unit 150 using classification. For example, the determination unit 150 may classify a class relating to the existence of a heart abnormality and another class relating to the nonexistence of a heart abnormality, thus making determination as to whether or not abnormality occurs in a heart.

In this connection, a classification of the determination unit 150 is not necessarily limited to a specific method, and therefore it is possible to employ various methods having learnability. For example, the determination unit 150 may perform classification using logistic regression or learning about output layers of reservoir computing; but this is not a restriction.

In addition, the determination unit 150 does not necessarily make determination using classification, and therefore the determination unit 150 may adopt various types of determination about the determination target 920. For example, it is possible to make quantitative determination about the determination target 920 such that the determination unit 150 may quantitatively evaluate a possibility of abnormality occurring in a heart.

The data $x\hat{}(t)$ can be expressed by Math. (4).

[Math. 4]

$$x^{\wedge}(t) = [x(t - P^{-}\Delta t), x(t - (P^{-} - 1)\Delta t), \ldots , x(t - \Delta t), x(t), x(t + \Delta t), \ldots , x(t + (P^{+} - 1)\Delta t), x(t + P^{+}\Delta t) \quad (4)$$

When the terms $x(t-P^{-}\Delta t)$ to $x(t+P^{+}\Delta t)$ each denoting the state of the state change unit 130 are expressed by column vectors, the symbol x^(t) may be expressed by a single column vector concatenating those column vectors.

In this connection, the time step for obtaining the state of the state change unit 130 used for determination of the determination unit 150 will be referred to as "attention". In FIG. 4, the symbol attention (t) can be expressed by Math. (5).

[Math. 5]

$$\text{attetion}(t) = [t - P^{-}\Delta t, t - (P^{-} - 1)\Delta t, \ldots , t - \Delta t, t, t + \Delta t, \ldots , t + (P^{+} - 1)\Delta t, t + P^{+}\Delta t] \quad (5)$$

In Math. (4), each of the terms $x(t-P^{-}\Delta t)$ to $x(t-\Delta t)$ denotes an example of the state of the state change unit 130 at the past time step before the reference time step t. In this connection, the symbol x(t) denotes an example of the state of the state change unit 130 at the reference time step t.

Each of the terms $x(t+\Delta t)$ to $x(t+P^{+}\Delta t)$ denotes an example of the state of the state change unit 130 at the future time step after the reference time step t.

According to Math. (4), the determination unit 150 may make determination based on the states of the state change unit 130 at the past time step before the reference time step t, the reference time step t, and the future time step after the reference time step t.

For example, the determination unit 150 may determine the existence/nonexistence of a heart abnormality based on the state of the state change unit 130 at each time step corresponding to one cycle of the heartrate variability. Due to the existence of a heart abnormality, it is expected that a symptom due to abnormality may occur in the state of the state change unit 130 at at least one time step or more.

Since the determination unit 150 makes determination at the time step responsive to a timing instruction signal from the reference-time-step identifying unit 120, it is expected that a similar symptom may occur in the state of the state change unit 130 at the time step having the same relative time counted from the reference time step for each cycle of heartrate variability. In this sense, it is expected that the determination unit 150 may perform determination with high accuracy.

Alternatively, the determination unit 150 may perform determination based on only the states of the state change unit 130 at the past reference time before the reference time step t and the reference time step t.

The determination unit 150 may perform determination based on only the states of the state change unit 130 at the reference time step t and the future time step after the reference time step t.

Alternatively, the determination unit 150 may perform determination based on only the state of the state change unit 130 at the past time step before the reference time step t.

The determination unit 150 may perform determination based on only the state of the state change unit 130 at the reference time step t.

The determination unit 150 may perform determination based on only the state of the state change unit 130 at the future time step after the reference time step 1.

To allow the determination unit 150 to perform determination according to the future time step after the reference time step t, one of or both the reference-time-step identifying unit 120 and the determination unit 150 may wait for time.

For example, the reference-time-step identifying unit 120 may output a timing instruction signal to the determination unit 150 at the time step $t+P^{+}\Delta t$ having passed $P^{+}$ time steps after the reference-time-step identifying unit 120 identifies the time step t as a reference time step.

Alternatively, the reference-time-step identifying unit 120 may output a timing instruction signal to the determination unit 150 at the reference time step t. Subsequently, the determination unit 150 may perform determination at the time step $t+P^{+}\Delta t$ having passed $P^{+}$ time steps after the reference time step t at which the determination unit 150 received the timing instruction signal.

The determination unit 150 may perform learning about the determination of the determination target 920 at a derivative time step from the reference time step.

Figure 5:
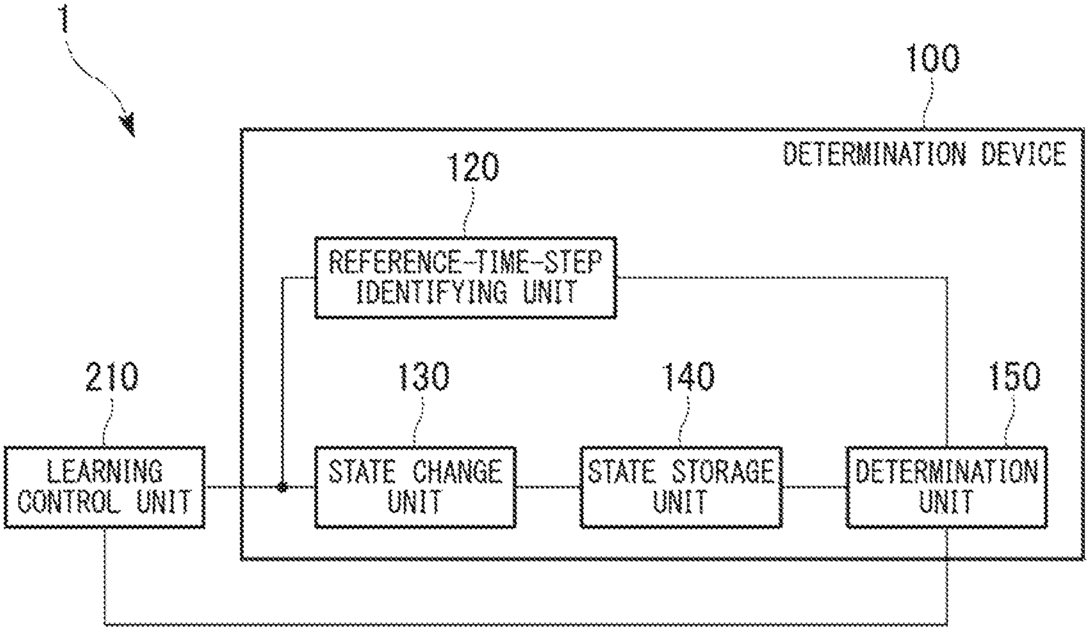
FIG. 5 shows a configuration example of a computation system 1 in which the determination unit 100 is configured to perform learning about a determination target 920.

FIG. 5 shows a configuration example of the computation system 1 configured to perform learning about the determination of the determination target 920 made by the determination device 100.

The configuration example of FIG. 5 differs from the configuration example of FIG. 1 in that a learning control unit 210 is substituted for the trigger-signal generation unit 910 and the determination target 920. In this connection, the learning control unit 210 may be formed as an independent device apart from the determination device 100 or as part of the determination device 100. A combination of the determination device 100 and the learning control unit 210 will be referred to as the computation system 1.

FIG. 5 shows a configuration example in which the learning control unit 210 is configured to input training data including sampling data of an electrocardiogram into the determination device 100 without using a sampling-data acquisition unit. In a learning mode, the determination device 100 may include or preclude the sampling-data acquisition unit 110.

As to other aspects, the configuration example of FIG. 5 is similar to the configuration example of FIG. 1.

The learning control unit 210 is configured to control learning about the determination of the determination unit 150. In particular, the learning control unit 210 may instruct the determination device 100 to perform learning about the determination of the determination unit 150 by providing to the determination device 100 the training data for each time step, which includes sampling data of an electrocardiogram and correct-answer label data indicating a correct answer of the determination result.

In this connection, the learning control unit 210 may store the training data. Alternatively, the learning control unit 210 may acquire training data from a database apparatus or other apparatuses.

The determination unit 150 is configured to perform learning based on the state of the state change unit 130 for one time step or more and the correct-answer label data acquired from the learning control unit 210. In particular, the determination unit 150 may perform learning at the time step having the same relative time as the relative time for determination counted from the time step for receiving a timing instruction signal from the reference-time-step identifying unit 120. Accordingly, it is expected that the determination unit 150 can perform learning with high accuracy.

In this connection, only the determination unit 150 among the state change unit 130 and the determination unit 150 may be subjected to learning. Accordingly, it is expected that a learning time may be relatively short.

In addition, the determination unit 150 may be formed using a single-layered neural network similar to an output layer of reservoir computing. Accordingly, it is expected that a learning time may be relatively short. Moreover, even when the determination unit 150 has a simple configuration such as a single-layered neural network, it is expected that learning can be performed with relatively high accuracy like the reservoir computing.

In this connection, we have obtained relatively good results in experiments about the determination device 100. In experiments, the determination device 100 was realized using software running on a computer, wherein heart abnormality sensing was performed using data sets of electrocardiograms.

In the above, five-hundred data were used as learning data while another five-hundred data were used as test data. Herein, each data is used in a first dimension including 2,000 steps, wherein first 200 steps among 2,000 steps were used for free-running. In addition, sinus-rhythm data were used as non-abnormal data. Furthermore, atrial-fibrillation data were used as abnormal data.

The state change unit 130 is formed as a reservoir layer with fifth neurons, wherein attention is set to time steps [−80, 60, . . . , 160, 180] in electrocardiogram data. In this connection, abnormality-sensing accuracy is 3.4% in learning while abnormality-sensing accuracy is 6.2 in testing.

As described above, the state change unit 130 may receive an input of data relating to the determination target 920 for each time step so as to change the state thereof for each time step. The reference-time-step identifying unit 120 is configured to identify a reference time step, i.e., a time step serving as the reference to the changing state of the determination target 920. The determination unit 150 is configured to make determination of the determination target 920 based on the state of the state change unit 130 at a derivative time step from the reference time step.

Since the state of the state change unit 130 is changed each time when inputting data relating to the determination target 920, it is expected that features of sampling data may appear in the state of the state change unit 130 even when features contributing to determination may appear in part of sampling data among time-series data representing a plurality of sampling data. In addition, the determination unit 150 is configured to make determination based on the state of the state change unit 130 at a derivative time step from the reference time step, and therefore it is possible to repeat determination with respect to the changing state of the determination target 920. In this sense, it is expected that the determination device 100 can perform determination with high accuracy.

As described above, the determination device 100 is able to handle the determination target 920 having time-series data serving as sampling data partly including features without using convolutional neural networks.

The reference-time-step identifying unit 120 may identify a reference time step as a time step in which data of the determination target 920 meets a predetermined condition.

That is, the determination unit 150 may perform determination based on the state of the state change unit 130 at a derivative time step from the reference time step, and therefore it is possible to repeat determination with respect to the changing state of the determination target 920 at similar timings. In this sense, it is expected that the determination device 100 can perform determination with high accuracy.

In addition, the reference-time-step identifying unit 120 may identify a reference time step as the time step associated with a time step at which the determination target 920 inputs signals from the outside of the determination target 920.

Since the determination unit 150 is configured to perform determination based on the state of the state change unit 130 at a derivative time step from the reference time step, it is possible to repeat determination with respect to the changing state of the determination target 920 at similar timings. In this sense, it is expected that the determination device 100 can perform determination with high accuracy.

In addition, the determination unit 150 may perform determination of the determination target 920 based on the state of the state change unit 130 at the past time step before the reference time step.

Accordingly, even when features contributing to determination may appear only in the sampling data at the past time step before the reference time step among time-series data representative of sampling data acquired by the sampling-data acquisition unit 110, it is expected that those features may easily appear in the state of the state change unit 130. In this sense, it is expected that the determination device 100 can perform determination with high accuracy.

In addition, the determination unit 150 may perform determination of the determination target 920 based on the state of the state change unit 130 at the future time step after the reference time step.

Accordingly, even when features contributing to determination may appear only in the sampling data at the future time step after the reference time step among time-series data representative of sampling data acquired by the sampling-data acquisition unit 110, it is expected that those features may easily appear in the state of the state change unit 130. In this sense, it is expected that the determination device 100 can perform determination with high accuracy.

The determination unit 150 is configured to perform learning about the determination of the determination target 920 at a derivative time step from the reference time step.

Accordingly, it is possible for the determination unit 150 to perform learning at time steps similar to those of determination in relation to the changing state of the determination target 920. That is, it is expected that the determination unit 150 can perform learning with high accuracy.

Figure 6:
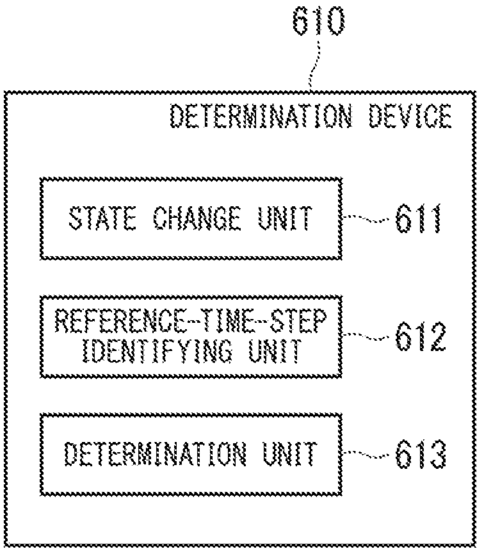
FIG. 6 shows another configuration example of a determination device according to an exemplary embodiment.

FIG. 6 shows a further configuration example of a determination device according to the exemplary embodiment. In the configuration example shown in FIG. 6, a determination device 610 includes a state change unit 611, a reference-time-step identifying unit 612, and a determination unit 613.

According to this configuration, upon receiving an input of data relating to a determination target for each time step, the state change unit 611 will be changed in state for each time step. The reference-time-step identifying unit 612 is configured to identify a reference time step as a time step serving as a reference to the changing state of a determination target. The determination unit 613 is configured to perform determination of a determination target based on the state of the state change unit 611 at a derivative time step from the reference time step.

Since the state of the state change unit 611 is changed each time when receiving an input of data relating to a determination target, even when features contributing to determination may appear only in part of sampling data among time-series data representative of sampling data relating to a determination target, it is expected that those features of sampling data may appear in the state of the state change unit 611. In addition, the determination unit 613 is configured to perform determination based on the state of the state change unit 611 at a derivative time step from the reference time step, and therefore it is possible to repeat determination with respect to the changing state of a determination target at similar timings. Accordingly, it is expected that the determination device 610 can perform determination with high accuracy.

As described above, it is possible for the determination device 610 to handle a determination target having time-series data representative of sampling data partly including features without using convolutional neural networks.

In this connection, the state change unit 611 may serve as an example of a state change means. The reference-time-step identifying unit 612 may serve as an example of a reference-time-step identifying means. The determination unit 613 may serve as an example of a determination means.

Figure 7:
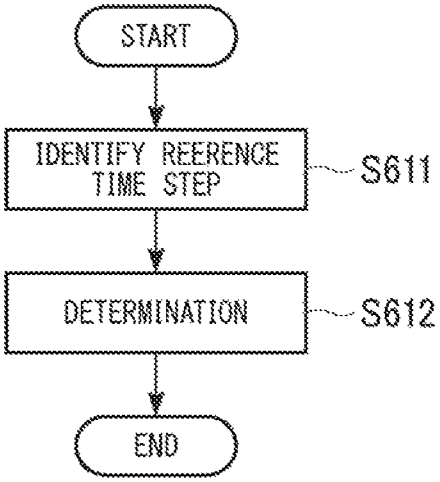
FIG. 7 is a flowchart showing an example of a procedure of steps in a determination method according to an exemplary embodiment.

FIG. 7 is a flowchart showing an example of a procedure according to a determination method of the exemplary embodiment. FIG. 7 shows an example of a procedure for determination with a device including a state change unit, which will be changed in state for each time step, upon receiving an input of data relating to a determination target for each time step. The determination method of FIG. 7 includes a step for identifying a reference time step (step S611) and a step for performing determination (step S612).

A step for identifying a reference time step (step S611) is to identify a reference time step, i.e., a time step serving as a reference to the changing state of a determination target.

A step for performing determination (step S612) is to perform determination of a determination target based on the state of a state change unit at a derivative time step from the reference time step. In this connection, the state change unit may serve as an example of a state change means.

Since the state change unit is changed each time when receiving an input of data relating to a determination target, even when features contributing to determination may appear only in part of sampling data among time-series of data representative of sampling data relating to a determination target, it is expected that those features may appear in the state of the state change unit. In addition, the foregoing process at step S612 is to perform determination based on the state of the state change unit at a derivative time step from the reference time step, and therefore it is possible to repeat determination with respect to the changing state of a determination target at similar timings. In this aspect, according to the determination method shown in FIG. 7, it is expected that determination can be carried out with high accuracy.

As described above, according to the determination method of FIG. 7, it is possible to handle a determination target having time-series of data representative of sampling data partly including features without using convolutional neural networks.

Figure 8:
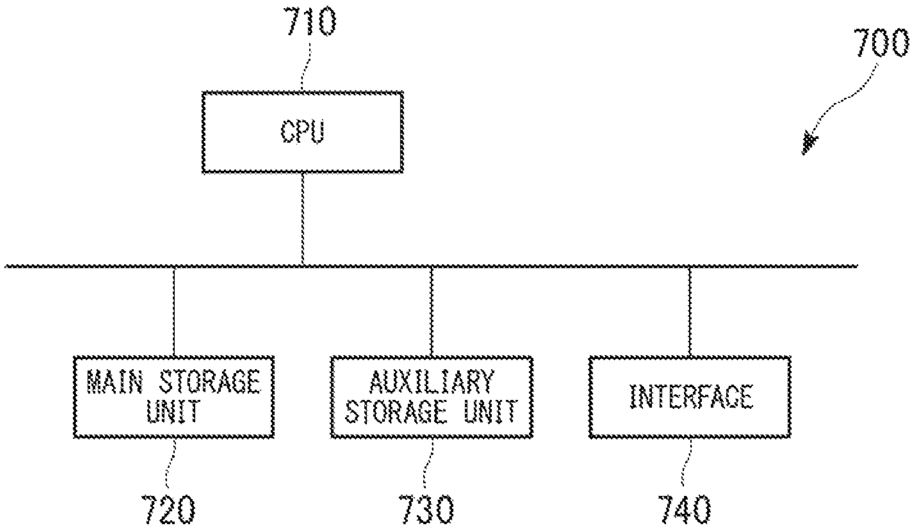
FIG. 8 is a block diagram showing the configuration of a computer according to at least one exemplary embodiment.

FIG. 8 is a block diagram showing the configuration of a computer according to at least one exemplary embodiment.

According to the configuration shown in FIG. 8, a computer 700 includes a CPU (Central Processing Unit) 710, a main storage unit 720, an auxiliary storage unit 730, and an interface 740.

At least one of or part of the determination device 100 and the determination device 610 may be implemented by the computer 700. In this case, a series of operations realized by the aforementioned processing units can be formulated as programs and stored on the auxiliary storage unit 730. The CPU 710 may read programs from the auxiliary storage unit 730 to expand programs on the main storage unit 720, thus executing the foregoing processes according to programs. In addition, the CPU 710 may secure storage areas corresponding to the aforementioned storage units on the main storage unit 720 according to programs. As to communication between each device and other devices, the interface 740 having a communication function can perform communication under the control of the CPU 710.

When the determination device 100 is installed in the computer 700, a series of operations relating to the sampling-data acquisition unit 110, the reference-time-step identifying unit 120, the state change unit 130, the state storage unit 140, and the determination unit 150 are formulated as programs and stored on the auxiliary storage unit 730. The CPU 710 may read programs from the auxiliary storage unit 730 to expand programs on the main storage unit 720, thus executing the foregoing processes according to programs.

In addition, the CPU 710 may secure storage areas such as the state storage unit 140 for the process of the determination device 100 on the main storage unit 720. As to communication between the determination device 100 and other devices, the interface 740 having a communication function may perform communication under the control of the CPU 710. As to user interaction with the determination device 100, the interface 740 equipped with a display device and an input device may display various types of images under the control of the CPU 710, thus executing reception of a user's operation.

When the determination device 610 is installed in the computer 700, a series of operations relating to the state change unit 611, the reference-time-step identifying unit 612, and the determination unit 613 are formulated as programs and stored on the auxiliary storage unit 730. The CPU 710 may read programs from the auxiliary storage unit 730 to expand programs on the main storage unit 720, thus executing the foregoing processes according to programs.

In addition, the CPU 710 may secure storage areas for the process of the determination device 610 on the main storage unit 720 according to programs. As to communication between the determination device 610 and other devices, the interface 740 having a communication function may perform communication under the control of the CPU 710. As to the user interaction with the determination device 610, the interface 740 equipped with a display device and an input device may display various types of images under the control of the CPU 710, thus executing reception of a user's operation.

In this connection, it is possible to store programs, which are used to execute the entirety or part of the foregoing processes realized by the determination device 100 and the determination device 610, on computer-readable storage media, wherein it is possible to achieve the foregoing processes by loading and executing programs stored on storage media with a computer system. Herein, the term "computer system" may include hardware such as peripheral devices and software such as an OS (Operating System).

In addition, the term "computer-readable storage media" refer to flexible disks, magneto-optical disks, ROM (Read-Only Memory), portable media such as CD-ROM (Compact-Disk Read-Only Memory), and storage units such as hard disks embedded in computer systems. The aforementioned programs may achieve part of the foregoing functions. Alternatively, the aforementioned programs may be differential programs (differential files) which can be combined with pre-installed programs of computer systems to achieve the foregoing functions.

Heretofore, the exemplary embodiment has been descried in detail with reference to the accompanying drawings, whereas concrete configurations should not be necessarily limited to the exemplary embodiment; hence, the present invention may include any types of designs without departing from the essence of the invention as defined in the appended claims.

INDUSTRIAL APPLICABILITY

The present invention is applicable to a determination device, a determination method, and a storage medium.

REFERENCE SIGNS LIST

1 Computation system
100, 610 Determination device
110 Sampling-data acquisition unit
120, 612 Reference-time-step identifying unit
130, 611 State change unit
140 State storage unit
150, 613 Determination unit
210 Learning control unit
910 Trigger-signal generation unit
920 Determination target

What is claimed is:

1. A determination device, comprising:
- a memory configured to store instructions and a model for receiving an input of electrocardiogram data for each of a plurality of time steps and for changing a state of the model for each of the time steps; and
- a processor configured to execute the instructions to:
  - identify a reference time step, of the plurality of time steps, as a reference to a changing state of a heart; and
  - determine, based on the state of the model at a derivative time step, of the plurality of time steps and from the reference time step, whether an abnormality of the heart exists,
- wherein identifying the reference time step comprises:
  - identifying, by comparing the value of the electrocardiogram data with a predetermined threshold value, a time step, of the plurality of time steps, in which a value of the electrocardiogram data is equal to or above the predetermined threshold value; and
  - setting the identified time step as the reference time step.

2. The determination device according to claim 1, wherein the processor is further configured to execute the instructions to identify the reference time step as for inputting the electrocardiogram data to the model.

3. The determination device according to claim 1, wherein the processor is further configured to execute the instructions to identify the reference time step for inputting a signal to the heart from an outside of the heart.

4. The determination device according to claim 1, wherein the processor is further configured to execute the instructions to determine, further based on a past state of the model at a past time step before the reference time step, whether the abnormality of the heart exists.

5. The determination device according to claim 1, wherein the processor is further configured to execute the instructions to determine, further based on a future state of the mode at a future time step that is after the reference time step, whether the abnormality of the heart exists.

6. The determination device according to claim 1, wherein the processor is further configured to execute the instructions to perform learning based on determining whether the abnormality of the heart exists at the derivative time step.

7. A determination method for a device that stores a model for receiving an input of electrocardiogram data for each of a plurality of time steps and for changing the a state of the model for each of the time steps, the method comprising:
- identifying a reference time step as a reference to a changing state of a heart; and
- determining, based on the state of the model at a derivative time step from the reference time step, whether an abnormality of the heart exists,
- wherein identifying the reference time step comprises:
  - identifying, by comparing the value of the electrocardiogram data with a predetermined threshold value, a time step in which a value of the electrocardiogram data is equal to or above the predetermined threshold value; and
  - setting the identified time step as the reference time step.

8. A non-transitory storage medium having a stored program causing a device that stores a model for receiving an input of electrocardiogram data for each of a plurality of time steps and for changing the a state of the model for each of the time steps to execute:
- identifying a reference time step, of the plurality of time steps, as a reference to a changing state of a heart; and
- determining, based on the state of the model at a derivative time step, of the plurality of time steps and from the reference time step, whether an abnormality of the heart exists,
- wherein identifying the reference time step comprises:
  - identifying, by comparing the value of the electrocardiogram data with a predetermined threshold value, a time step, of the plurality of time steps, in which a value of the electrocardiogram data is equal to or above the predetermined threshold value; and
  - setting the identified time step as the reference time step.

9. The determination device according to claim 1, wherein the model comprises a reservoir layer of a recurrent neural network configured to store past states of the model, and determining whether the abnormality of the heart exists is further based on concatenated state data from ones of the plurality of time steps relative to the reference time step, the concatenated state data comprises states of the model at the ones of the plurality of time steps.

* * * * *